United States Patent [19]

Wales et al.

[11] Patent Number: 4,951,223
[45] Date of Patent: Aug. 21, 1990

[54] WEB MATERIAL INSPECTION SYSTEM

[76] Inventors: R. Langdon Wales, Moccasin Hill, Lincoln, Mass. 01773; H. W. Crowley, 310 Parker, Newton, Mass. 02159

[21] Appl. No.: 441,174

[22] Filed: Nov. 27, 1989

Related U.S. Application Data

[63] Continuation of Ser. No. 329,445, Mar. 28, 1989, abandoned, which is a continuation of Ser. No. 149,683, Jan. 28, 1988, abandoned.

[51] Int. Cl.⁵ .................. G06F 15/46; G01B 11/30
[52] U.S. Cl. .................. 364/507; 101/248; 101/486; 358/106; 358/107
[58] Field of Search ............. 364/507; 358/101, 106, 358/107; 250/559–563; 101/181, 491

[56] References Cited

U.S. PATENT DOCUMENTS

| | | | |
|---|---|---|---|
| 3,696,577 | 7/1976 | Lloyd et al. | 358/106 |
| 3,988,530 | 10/1976 | Ikegami et al. | 250/562 X |
| 4,009,814 | 3/1977 | Singh | 226/113 |
| 4,232,336 | 11/1980 | Henry | 358/106 |
| 4,389,669 | 6/1983 | Epstein et al. | 358/106 |
| 4,403,294 | 9/1983 | Hamada et al. | 364/507 |
| 4,428,287 | 1/1984 | Greiner | 101/248 |
| 4,437,403 | 3/1984 | Greiner | 101/248 |
| 4,570,180 | 2/1986 | Baier et al. | 358/106 |
| 4,578,770 | 3/1986 | Mitani | 250/562 X |
| 4,583,181 | 4/1986 | Gerber et al. | 364/507 X |
| 4,665,317 | 5/1987 | Ferriere et al. | 250/562 |
| 4,736,680 | 4/1988 | Wales et al. | 101/491 |

FOREIGN PATENT DOCUMENTS 2181834 4/1987 United Kingdom ........... 364/507

Primary Examiner—Felix D. Gruber
Attorney, Agent, or Firm—Wolf, Greenfield & Sacks

[57] ABSTRACT

A system for inspecting and characterizing continuous web material such as may be wound into a roll. This system includes a recording storage means for providing a duplicate image of the web material and a device for reviewing the recording storage means image to detect a predetermined characterisitc of the image such as a defect therein. The position along the image is detected and a switch is responsive to both the content information and position information to record an indicia of image position corresponding to detection of the predetermined characteristic.

29 Claims, 5 Drawing Sheets

| DEFECT LIST ||
|---|---|
| NO. | FRAME |
| 1. | 25 |
| 2. | 26 |
| 3. | 27 |
| 4. | 329 |
| 5. | 410 |
| 6. | 411 |
| ⋮ | ⋮ |

*Fig.3*

WEB MATERIAL INSPECTION SYSTEM

This application is a division of application Ser. No. 07/329,445, filed Mar. 28, 1989 which in turn is a continuation of Ser. No. 07/149,638 filed Jan. 28, 1988 both now abandoned.

BACKGROUND OF THE INVENTION

I. Field of the Invention

The present invention relates in general to a web material inspection system. More particularly, the present invention relates to an inspection and characterizing system for web material involving the forming of a duplicate image of, in particular newly produced material, onto another medium that can be readily accessed and inspected.

II. Background Discussion

Continuously processed material such as continuous web material typically in a paper form is many times stored in a roll form. During a manufacturing process the material that is produced may include defects or it may be desired to determine the position of certain indicia on the continuous material. At the present time there is no known effective technique for inspecting for defects or for identifying certain characteristics of the continuous material, such as certain printed text thereon.

In the case of web material being fed, such as paper web material being fed from say a laser printer, the manufacturing process is carried out quite rapidly and it is difficult to provide any reasonable type of human inspection. Furthermore, because the continuous material is usually wound into a roll, it makes the material generally inaccessible and thus it cannot be inspected without unwinding the roll.

Accordingly, it is an object of the present invention to provide a technique for web material inspection to record defects in the continuous material and in particular the position in the roll of such defects. A related object of the invention is to also provide for the inspection of continuous material for the purpose of identifying predetermined characteristics of the continuous material and/or predetermined characteristics of images thereon.

SUMMARY OF THE INVENTION

In accordance with the present invention, means are provided for preferably continuously sensing the material as it passes from a manufacturing processing stage and making a duplicate image of the newly produced material. This image is recorded on a medium such as, for example, video tape that can be subsequently accessed and inspected. This inspection can be carried out separately from the web material processing. The inspection can be furthermore carried out faster and easier than attempting to inspect the actual product itself.

In accordance with the present invention, there is provided a system for inspecting and characterizing continuous material such as may be wound into a roll. The system comprises a recording storage means for providing a duplicate image of the web material. Means are provided for reviewing the recording storage means image to detect a predetermined characteristic of the image. This predetermined characteristic may be a defect in the image. Means are provided for detecting the position along the image as recording storage means image is reviewed. Means are provided responsive to the predetermined characteristic of the image being detected to record an indicia of image position corresponding to detection of said predetermine characteristic.

In accordance with further features of the present invention, the recording storage means may include a video camera for recording the image on a video tape. A camera means may be disposed adjacent the web material for capturing the image on a continuous basis and coupling it to the recording storage means. The recording storage means may be comprised of optical means such as an optical scanner and associated film for recording the image. In a further embodiment of the present invention the recording storage means may include image detection means and memory storage means for the detected image. The storage means may alternatively comprise magnetic storage means. The storage means may also include digital storage means or analog storage means. The duplicate image may be separated into frames corresponding to web material frames each having a position marker or the like associated therewith. The means for detecting the position along the image may include means for counting markers to determine position. Alternatively, a means may be provided for essentially counting the length of the web material to determine position. In connection with detecting a defect means may be provided for establishing a reference image in combination with means for comparing the detected image with the desired reference image to thus detect a defect. Once the defect is detected then the corresponding position information is immediately latched. For this purpose a switch means may be provided. The final position is corresponding to defects or other predetermined characteristics of the continuous material recorded on a recording medium which may be in the form of a printer output that provides a listing of roll locations of interest.

BRIEF DESCRIPTION OF THE DRAWINGS

Numerous other objects, features, and advantages of the invention should now become apparent upon a reading of the following detailed description taken in conjunction with the accompanying drawings, in which:

FIG. 3 illustrates a representative output recording medium format;

DETAILED DESCRIPTION

The present invention relates to the inspection and characterizing of continuous material, such as continuous web material typically a paper web that is wound into a roll. For example, during a manufacturing process such as a printing process on web material certain defects may occur. The present invention is a means by which these defects can be recorded as to their position in the roll. A duplicate image of the newly produced material is made and is recorded onto another medium such as video tape. This can then be accessed and inspected faster and easier than the inspection of the actual product.

Figure 1:
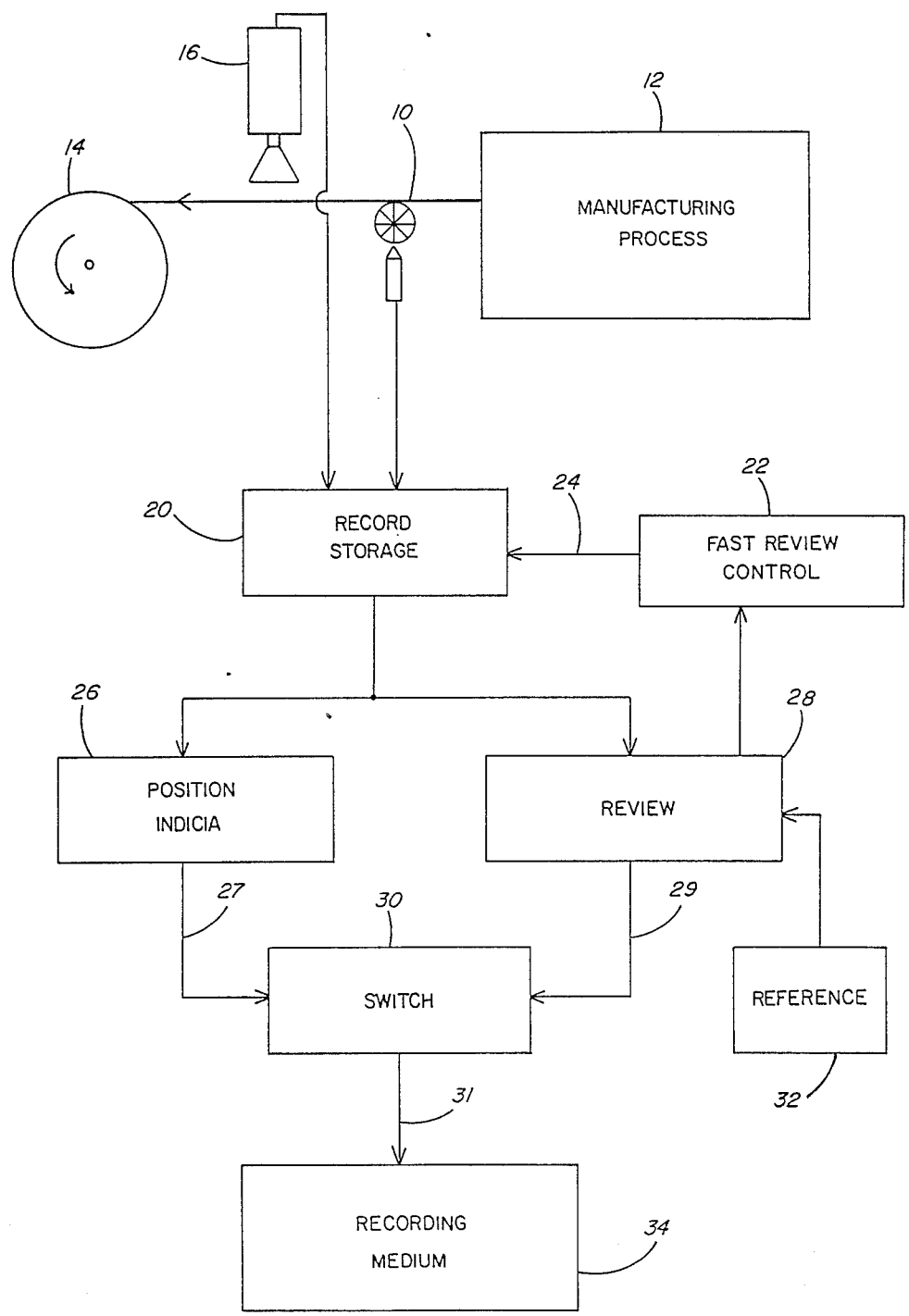
FIG. 1 is a block diagram of a system in accordance with the present.

Now, reference is made to one embodiment of the present invention as illustrated in the block diagram of FIG. 1. FIG. 1 illustrates web material at 10 coming from a manufacturing process identified by the block 12 in FIG. 1. This manufacturing process may be, for example, a printing press or a laser printer upon which a certain text is printed, refer to herein as an image on the continuous material. FIG. 1 also shows the web material being wound into a roll 14.

The embodiment being described herein in FIGS. 1–3 will be explained primarily in association with the detection of defects in the continuous material. However, it is understood that the concepts of the invention may also be employed in detecting other predetermined characteristics of the continuous material. For example, if one is printing forms on the web material then it may be desired to pinpoint locations of certain predetermined formats of forms on the roll.

Figure 2:
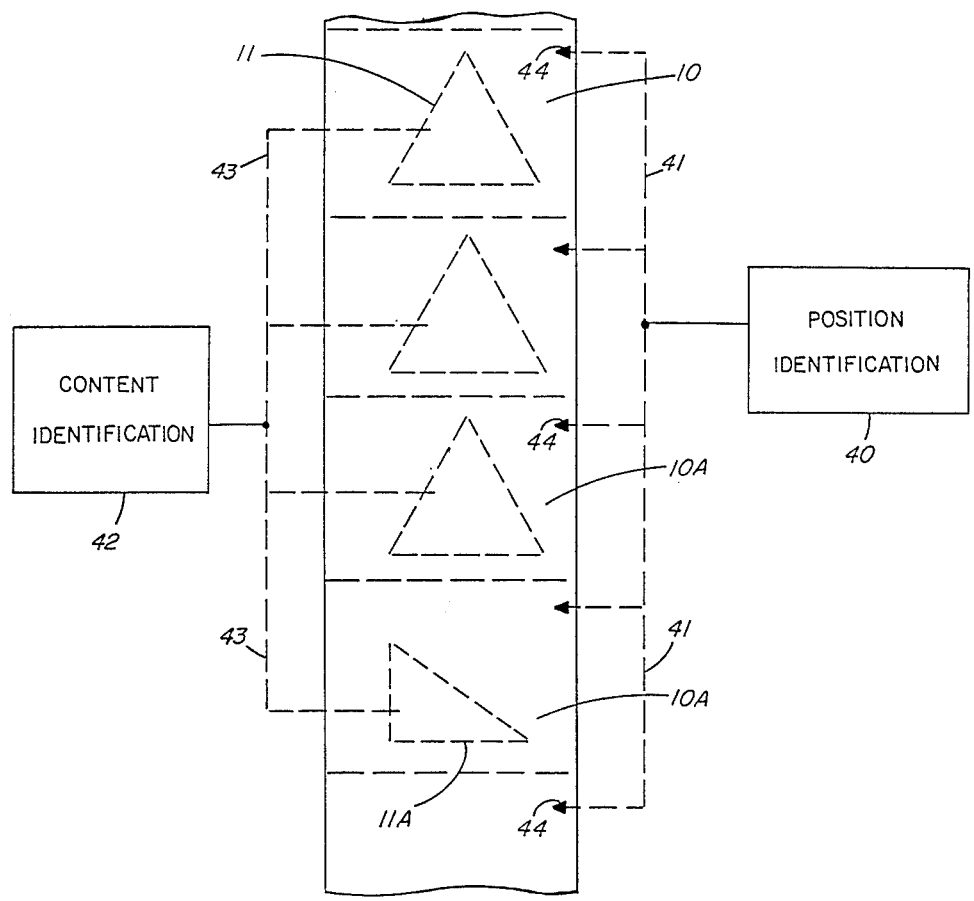
FIG. 2 is a schematic representation of the continuous material illustrating successive images and position markers.
Figure 4:
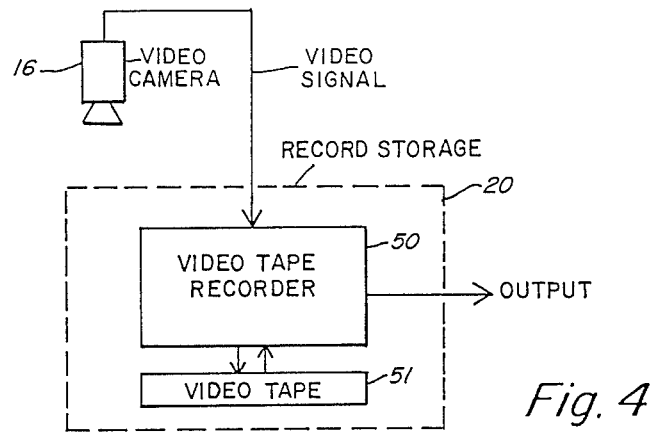
FIG. 4 is a more detailed block diagram of the record storage function of FIG. 1.

FIG. 1 represents an embodiment in which the image on the web material 10 is duplicated by means of a video camera 16 which, as shown in FIG. 2, is connected to a recorder 50 for recording on a video tape 51. This embodiment is generally represented in FIG. 1 by the record storage box 20. If the web material is coming from a printing press then a video camera may be adapted to be controlled with a strobe to record each press impression onto the video tape.

The diagram of FIG. 1 also illustrates the fast review control box 22 that has an output control line 24 coupling to the record storage 20. In a manual mode of operation in accordance with the invention an operator can periodically rewind the tape by means of manual control via the control box 22 to inspect the stored images in a fast rewind mode of operation. In this manual operator mode of operation, if defects are found the particular position along the tape can be noted for subsequent operations, such as to remove the defective material. The position on the tape of the detected defect may be identified by a particular coded marking on the tape, in the case of a video tape, or can be identified by its particular position on the video tape. In this regard the fast review manual made may include a counter or timer that identifies the particular position on the video tape. This may identify in terms of an actual frame or impression on the video tape or may be identified in terms of a time sequence from the beginning of the tape when the tape is reviewed at a normal speed.

Figure 5:
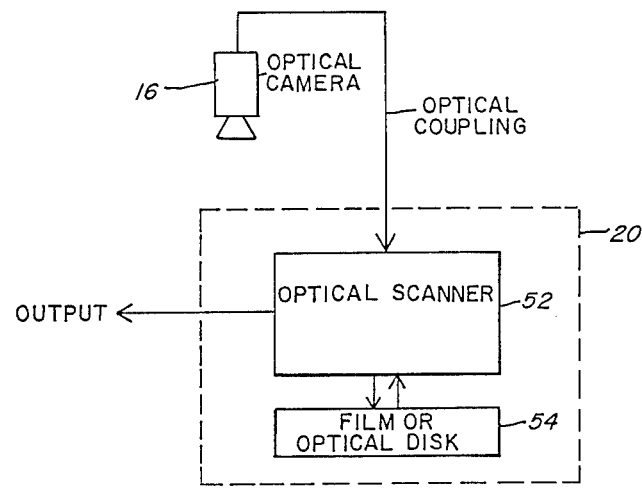
FIG. 5 is a more detailed block diagram of an optical embodiment for the record storage function of FIG. 1.

In the disclosed embodiment, the means for providing a duplicate of the image has been described as video means in the form of a video camera and associated video tape. However, the image can also be stored on other mediums either optically or by other recording techniques. Optically the image can also be stored by means of an optical scanner 52 as shown in FIG. 5, on film or optical disks 54.

Figure 6:
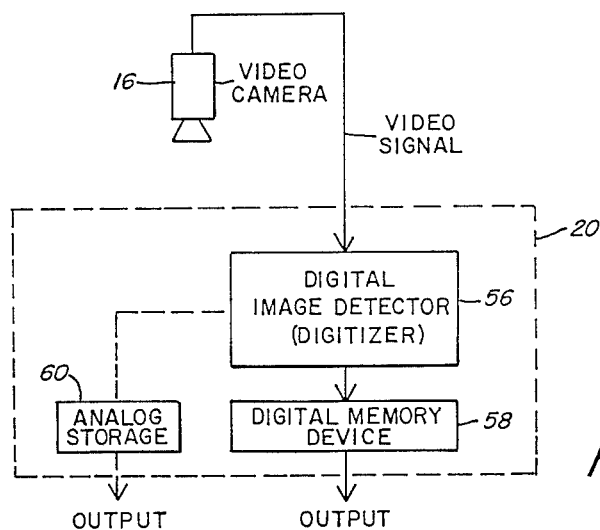
FIG. 6 is a more detailed block diagram of a digital embodiment for the record storage function of FIG. 1.

In another embodiment, as described in FIG. 6, the image can be digitized through use of a digital image detector 56 and stored by a digital memory device 58 that uses magnetic disks or cards. The storage of memory can be in analog form 60 as well as in digital form.

The system of the present invention stores the images in a convenient medium that allows fast and easy inspection and position identification of certain characteristics of the product. These characteristics can be measured in motion and compared with a standard to detect deviations, such as printing defects. The inspection can be carried out by an operator as described previously or can be carried out automatically as to be described in further detail hereinafter. Generally speaking, the position identification can be carried out by counting images, counting holes in the film or computer form paper, measuring linear distance by coded marks on the material to be inspected, or by sequential position measurement.

With further reference to FIG. 1, it is noted that the record storage box 20 couples to the position indicia box 26 as well as to the review box 28. It is also noted that the review box 28 intercouples with the fast review control box 22. Also provided is a reference box 32 that couples to the review box 28. Basically, the position indicia box 26 is detecting position identification regarding the recording medium while the review box 28 is reviewing the content of the images on the recording medium.

Figure 7:
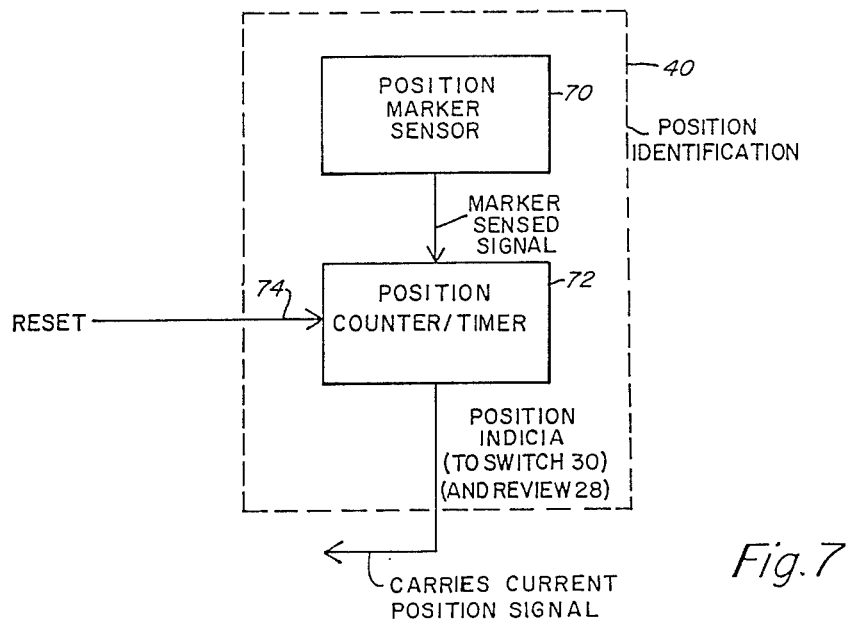
FIG. 7 is a more detailed block diagram of the position identification function of FIG. 2.

Reference is now made, with respect to content and position identification, to the diagram of FIG. 2. FIG. 2 shows the web material 1? such as coming from a printing press being separated into separate press impressions 10A. Each of these press impressions has an illustrative image printed thereon such as illustrated at 11 in the FIG. 2 In FIG. 2 there is also shown the position identification box 40 and the content identification box 42. The position identification box 40 of FIG. 2 relates to the position indicia box 26 of FIG. 1. The content identification box 42 of FIG. 2 corresponds to the review box 28 of FIG. 1. It is noted that the position identification box 40 illustrates by output lines 41 the sensing of the markers 44 associated with each of the press impressions 10A. The position identification box 40 as well as the position indicia box 26 of FIG. 1 may be adapted to count these markers 44 to keep track of position along the web material. In this regard, the position identification 40 may, as shown in FIG. 7, may include a counter or timer 72 that is resettable by a signal 74 upon the initial start of each manufacturing subprocess for printing onto a roll.

FIG. 2 also illustrates the content identification box 42 having associated therewith output lines 43 that are illustrated in FIG. 2 as essentially sensing certain characteristics regarding the images impressed on the web material. It is noted that one of the images 11A is represented as being faulty because it does not correspond in shape with the other images 11. It is the purpose of the content identification box 42 to ascertain such a defect.

Figure 8:
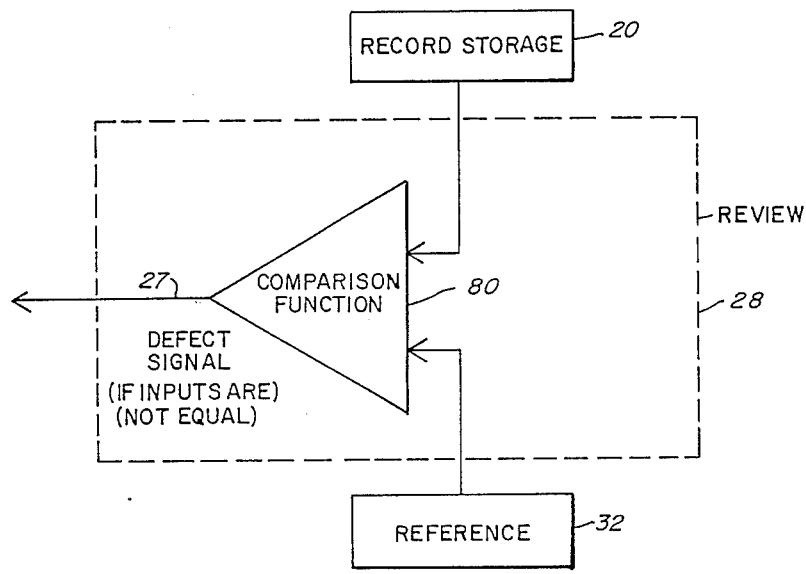
FIG. 8 is a more detailed block diagram of the review function of FIG. 1.

Now, reference is again made to FIG. 1 and the reference box 32. The reference box 32 establishes the reference against which the recording medium image is compared. When the comparison 80, as depicted in FIG. 8, is not proper or in other words when a defect of some type is detected then there i$ an output from the review box 28 at line 29 coupling to the switch 30. A detection of a defect by the review of inspection box 28 in FIG. 1 generates a signal on line 29 to essentially enable the switch 30. It is furthermore noted that the switch 30 receives a signal on line 27 from the position indicia box 26. The output of switch 30 at line 31 couples to the recording medium 34.

The switch 30 is basically enabled from line 29 and adapted to pass the information on line 27 to line 31 when so enabled. In the example illustrated in FIG. 2, when the image 11A is detected by the review box 28 as being a defective image, the switch 30 is enabled via line 29. The position information at line 27 at that very time is thus coupled via the switch 30 to line 31 and to the recording medium 34. In other words, there is recorded on the recording medium 34 an indication of a defective location or locations in the roll. This indication is by means of position identification. In this regard refer to FIG. 3 that shows a typical format for the recording medium 34. The recording medium 34 may be a paper printout or may be of other form. The defect list illustrated in FIG. 3 illustrates sequential defects and identifies them by a frame number which may correspond to a count corresponding to the number of markers counted. This then identifies the position within the roll that he defect occurs. In the particular example illustrated in FIG. 3, there are defects detected at frames 25-27, 329, 410, and 411.

Thus, the recording medium 34 essentially provides a list of defects in the particular example given in connection with the printing operation. In addition to the detection of defects, the system of the present invention can also detect certain predetermined characteristics of the image. As a matter of fact, the concepts of the present invention may even be employed in detecting defects in web material that has not been printed upon but that is coming directly from a paper manufacturing process. For example, there may be certain impressions in the printing process that one would like to identify as to position on he roll. By establishing a reference in making the comparison previously described, one can then determine at what position this particular image appears. These position readings are then recorded on the recording medium 34. This would not be in the form of a defect list but instead would be in the form of a list for identifying predetermined characteristics.

In summary, in accordance with the present invention, there is provided an information storage medium that has a sequential correspondence with the product and that is used to store the desired product quality information for subsequent analysis of characteristics of the product. The product characterization is stored on preferably a compact medium and may be kept with the product for subsequent use of the characterizing information in deciding on the manner of use of the product or of rejection of unacceptable product at the time the material is released from its storage state.

Having now described a limited number of embodiments of the present invention, it should now be apparent to those skilled in the art that numerous other embodiments and modifications thereof are contemplated within the scope of the present invention as defined by the appended claims.

What is claimed is:

1. A system for inspecting and characterizing a continuous web material such as may lie wound into a roll, said system comprising recording storage means for providing a duplicate image of the web material, means for reviewing the recording storage means image to detect a predetermined characteristic of the image, means for determining a position along said image as the image is reviewed, and means responsive to the predetermined characteristic of the image being detected to record an indicia of image position corresponding to detection of said predetermined characteristic.

2. A system as described in claim 1 wherein said recording storage means includes a video camera for recording the image on a video tape.

3. A system as described in claim 1 including camera means disposed adjacent said web material for capturing the image on a continuous basis and coupling to said recording storage means.

4. A system as described in claim 3 wherein said recording storage means comprises optical means.

5. A system as described in claim 4 wherein said optical means comprises an optical scanner and film for recording the image.

6. A system as described in claim 1 wherein said recording storage means includes image detection means and memory storage means for the detected image.

7. A system as described in claim 6 wherein said storage means comprises magnetic storage means.

8. A system as described in claim 6 wherein said storage means includes digital storage means.

9. A system as described in claim 6 wherein said storage means includes analog storage means.

10. A system as described in claim 1 wherein said means for reviewing comprises means for detecting a defect in said image.

11. A system as described in claim 10 wherein the duplicate image is separated into frames corresponding to web material frames each having a position marker associated therewith.

12. A system as described in claim 11 wherein said means for determining the position along said image includes means for counting markers to determining position.

13. A system as described in claim 1 wherein said means for reviewing comprises means for detecting a defect in the image including means for establishing a reference image and means for comparing the detected image with the desired reference image to detect defects.

14. A system as described in claim 1 wherein said means to record an indicia of image position includes a recording medium and means responsive to detection of said predetermined characteristic to pass the corresponding indicia to said recording medium.

15. A system as described in claim 14 wherein said means to pass includes switch means.

16. A system as described in claim 15 wherein said predetermined characteristic is a defect in the web material.

17. A method for inspecting and characterizing continuous product including the steps of recording a duplicate image of the product in a recording storage means, reviewing the recording storage means image to detect a predetermined characteristic of the image, determining a position along the image as the image is reviewed and recording an indicia of image position upon detection of said predetermined characteristic of the image and corresponding to detection of said predetermined characteristic.

18. A method as set forth in claim 17 wherein the step of duplicating the image includes video recording the image.

19. A method as set forth in claim 17 wherein the step of duplicating the image includes optically storing the image.

20. A method as set forth in claim 17 wherein the step of reviewing includes detecting a defect in the image.

21. A method as set forth in claim 17 wherein the step of determining the position includes counting markers on the product to determine position.

22. A method as set forth in claim 17 wherein the step of reviewing the image includes establishing a reference image and comparing the detected image with the reference image.

23. A system for inspecting and characterizing web material comprising means for storing a duplicate image of indicia of the web material, means for reviewing the stored image to detect a predetermined characteristic thereof, means for determining positions along the image as the image is reviewed, and means responsive to the predetermined characteristic of the image that is detected to record and indicia of image position corresponding to detection of said predetermined characteristic.

24. A system as described in claim 23 wherein said means for reviewing comprises means for detecting a defect in the image including means for establishing a reference image and means for comprising the detected image with the desired reference image to detect defects.

25. A system as described in claim 23 wherein said means to record an indicia of image position includes a recording medium and means responsive to detection of said predetermined characteristic to pass the corresponding indicia to said recording medium.

26. A system as described in claim 23 including camera means disposed adjacent to said web material for capturing the image on a continuous basis and coupling to said recording storage means.

27. A system as described in claim 26 wherein said recording storage means comprises optical means.

28. A system as described in claim 27 wherein said optical means comprises an optical scanner and film for recording the image.

29. A system as described in claim 23 wherein said recording storage means includes image detection means and memory storage means for the detected image.

* * * * *